United States Patent
Behling

(10) Patent No.: US 10,660,595 B2
(45) Date of Patent: May 26, 2020

(54) APPARATUS FOR X-RAY IMAGING AN OBJECT

(71) Applicant: KONINKLIJKE PHILIPS N.V., Eindhoven (NL)

(72) Inventor: Rolf Karl Otto Behling, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/309,956

(22) PCT Filed: Jun. 16, 2017

(86) PCT No.: PCT/EP2017/064788
§ 371 (c)(1),
(2) Date: Dec. 14, 2018

(87) PCT Pub. No.: WO2017/216354
PCT Pub. Date: Dec. 21, 2017

(65) Prior Publication Data
US 2019/0159742 A1 May 30, 2019

(30) Foreign Application Priority Data
Jun. 16, 2016 (EP) .................................... 16174828

(51) Int. Cl.
*G01N 23/04* (2018.01)
*A61B 6/00* (2006.01)
*G01N 23/041* (2018.01)

(52) U.S. Cl.
CPC ............ *A61B 6/484* (2013.01); *A61B 6/4007* (2013.01); *A61B 6/4021* (2013.01);
(Continued)

(58) Field of Classification Search
CPC ............ G01N 23/041; G21K 2207/005; A61B 6/484; A61B 6/584; A61B 6/502;
(Continued)

(56) References Cited

U.S. PATENT DOCUMENTS 8,995,614 B2 * 3/2015 Nagatsuka ............. A61B 6/463
378/62
9,001,969 B2 * 4/2015 Murakoshi ........... A61B 6/4233
378/70
(Continued)

FOREIGN PATENT DOCUMENTS

WO WO2010150136 A1 12/2010
WO WO2014125389 A1 8/2014

OTHER PUBLICATIONS

Pfeiffer, F. et al., "Phase Retrieval and Differential Phase-Contrast Imaging with Low-Brilliance X-Ray Sources", Nature Physics, vol. 2, pp. 258-261, Apr. 2006.
(Continued)

*Primary Examiner* — Kiho Kim
(74) *Attorney, Agent, or Firm* — Larry Liberchuk

(57) ABSTRACT

The present invention relates to an apparatus (10) for imaging an object. It is described to position (210) an X-ray detector relative to at least one X-ray source such that at least a part of a region between the at least one X-ray source and the X-ray detector is an examination region for accommodating an object. In a first mode of operation, with the at least one X-ray source a first focal spot is produced (220), such that at least some first X-rays produced at the first focal spot pass through a first grating of an interferometer arrangement, the first grating positioned at a first position, and such that the at least some first X-rays pass through a second grating of the interferometer arrangement, the second grating positioned at a second position. In the first mode of operation, the at least some first X-rays are detected (230) with the X-ray detector at a detector position. In a second mode of operation, with the at least one X-ray source a second focal spot is produced (240), such that at least some second X-rays produced at the second focal spot avoid the first grating at the first position. In the second mode of
(Continued)

operation, the at least some second X-rays are detected (250) with the X-ray detector at the detector position.

15 Claims, 4 Drawing Sheets

(52) U.S. Cl.
CPC ............ *A61B 6/4291* (2013.01); *A61B 6/502* (2013.01); *A61B 6/584* (2013.01); *G01N 23/041* (2018.02); *A61B 6/482* (2013.01); *G21K 2207/005* (2013.01)

(58) Field of Classification Search
CPC ... A61B 6/4291; A61B 6/4021; A61B 6/4007; A61B 6/483
See application file for complete search history.

(56) References Cited

U.S. PATENT DOCUMENTS

| | | | |
|---|---|---|---|
| 9,025,725 B2* | 5/2015 | Kiyohara | ................. A61B 6/06 378/197 |
| 9,025,726 B2* | 5/2015 | Ishii | ....................... A61B 6/484 378/62 |
| 9,135,728 B2* | 9/2015 | Fan | .......................... A61B 6/06 |
| 2007/0183559 A1 | 8/2007 | Hempel | |
| 2007/0183560 A1 | 8/2007 | Popescu | |
| 2009/0154640 A1 | 6/2009 | Baumann | |
| 2013/0235973 A1* | 9/2013 | Murakoshi | ........... A61B 6/4233 378/37 |
| 2013/0308750 A1* | 11/2013 | Ishii | ..................... A61B 6/4233 378/36 |
| 2014/0169522 A1* | 6/2014 | Hoshino | ................ A61B 6/484 378/36 |
| 2016/0338659 A1* | 11/2016 | Hoshino | .................. A61B 6/04 |

OTHER PUBLICATIONS

Roessl, E. et al., "Clinical Boundary Conditions for Grating-Based Differential Phase-Contrast Mammography", Philosophical Transactions of the Royal Society A, vol. 372, pp. 1-15, Jan. 2014.
Weber T. et al., "Report of Improved Performance in Talbot-Lau Phase-Contrast Computed Tomography", Medical Physics Letters, vol. 42, issue 6, pp. 2892-2896, Jun. 2015.

* cited by examiner

APPARATUS FOR X-RAY IMAGING AN OBJECT

FIELD OF THE INVENTION

The present invention relates to an apparatus for X-ray imaging an object, to a system for X-ray imaging an object, and to a method for X-ray imaging an object, as well as to a computer program element and a computer readable medium.

BACKGROUND OF THE INVENTION

Differential phase contrast and dark-field imaging (DPCI and DFI) are promising technologies that will likely add additional diagnostic value e.g. for mammography or for pre-clinical application with small animals, in addition to attenuation imaging. A conventional X-ray source can be used with a Talbot-Lau interferometer and a conventional X-ray detector. However, in a class of tasks where DPCI and DFI is not required, the interferometer is moved out of the beamline. This is cumbersome, and can lead to misalignment issues when the interferometer is moved back again when DPCI and DFI are again required.

US2007/0183559A1 discloses an X-ray CT system is for producing tomographic phase contrast and absorption images wherein the gratings for phase contrast are displaced accordingly.

SUMMARY OF THE INVENTION

It would be advantageous to have an improved technology for providing dark field and/or phase contrast images in combination with providing conventional attenuation images.

The object of the present invention is solved with the subject matter of the independent claims, wherein further embodiments are incorporated in the dependent claims. It should be noted that the following described aspects of the invention apply also for the apparatus for X-ray imaging an object, system for X-ray imaging an object and the method for X-ray imaging an object, and for the computer program element and the computer readable medium.

According to a first aspect, there is provided an apparatus for X-ray imaging an object, comprising:

at least one X-ray source;
 an X-ray interferometer arrangement; and
 an X-ray detector.

The X-ray detector is configured to be positioned relative to the at least one X-ray source such that at least a part of a region between the at least one X-ray source and the X-ray detector is an examination region for accommodating an object. The X-ray interferometer arrangement comprises a first grating and a second grating. In a first mode of operation the at least one X-ray source is configured to produce a first focal spot. The at least one X-ray source is configured to produce X-rays such that at least some first X-rays produced at the first focal spot pass through the first grating at a first position and pass through the second grating at a second position. The X-ray detector at a detector position is configured to detect the at least some first X-rays. In a second mode of operation the at least one X-ray source is configured to produce a second focal spot. The at least one X-ray source is configured to produce X-rays such that at least some second X-rays produced at the second focal spot avoid the first grating at the first position. The X-ray detector at the detector position is configured to detect the at least some second X-rays.

In other words with a first focal spot X-rays can be sent through an object and pass through an interferometer arrangement and be detected by a detector in order to provide Differential Phase Contrast Imaging (DPCI) and/or Dark Field Imaging (DFI). Then, an extra focal spot provided, which can be electronically switched by electric or magnetic means like grid switching or magnetic deflection of an electron beam or by any combination thereof to generate X-radiation at a different position such that X-rays can be sent through the object and be detected by the detector at the same position, and the X-rays avoid at least one of the gratings of the interferometer arrangement with no movement of the at least one grating being required. This enables switching from a DPCI/DFI mode of operation to a conventional attenuation imaging mode of operation, without movement of the at least one grating being required, facilitated through electronic switching of the focal spot position.

In this manner, mechanical simplicity is provided as the first grating does not have to be moved when switching from a DPCI/DFI mode of operation to an attenuation mode of operation.

To put this another way, the at least one grating does not have to be mechanically moved when "switching off" the DPCI/DFI function in an X-ray apparatus. In this way, by electronically switching focal spot positions, at least one grating structure is bypassed enabling the apparatus to switch from a DPCI/DFI mode using a single detector at a fixed position.

In an example, the first grating at the first position is positioned between the examination region and the first focal spot.

In this manner, mechanical simplicity is provided in that no mechanical movement mechanism is required on the source side of the examination region, for the movement of the first grating. This frees up space on this side of the examination region. Furthermore, by having the first grating on this side of the examination region the second focal spot does not have to be as far spaced from the first focal spot in order to avoid the first grating than if the first grating was on the far side of the examination region. Alternatively, or additionally, the first diffraction grating can be larger that it could be if it was positioned on the far side of the examination region.

In an example, in the second mode of operation the at least some second X-rays avoid the second grating at the second position.

In this manner, further mechanical simplicity is provided as neither the first nor the second diffraction grating have to be moved in switching from, for example a DPCI/DFI mode of operation to an attenuation mode of operation.

In an example, the second grating at the second position is positioned between the first grating at the first position and the examination region.

In this manner, mechanical simplicity is provided in that no mechanical movement mechanism is required on the source side of the examination region, for the movement of gratings. This frees up space on this side of the examination region as no movement mechanism is required. Furthermore, by having the second grating on this side of the examination region the second focal spot does not have to be as far spaced from the first focal spot in order to avoid the first and second gratings. Alternatively, or additionally, the second diffraction grating can be larger that it could be if it was positioned on the far side of the examination region.

In an example, in the second mode of operation the second grating is configured to be positioned at a position other than the second position, and wherein the at least some second X-rays produced at the second focal spot avoid the second grating at the position other than the second position.

In other words, in the second mode of operation the second grating is moved out of the way in order that X-rays do not pass through it and then the apparatus can operate in a conventional attenuation modality.

Thus electronic switching of the position of focal spots, combined with movement of one grating, enables the modality of the apparatus to be changed from, for example, a DPCI/DFI mode to an attenuation mode with reduced mechanical complexity because the at least one grating and the detector are not moved.

In an example, the X-ray interferometer arrangement comprises a third grating. In the first mode of operation the at least some first X-rays produced at the first focal spot pass through the third grating at a third position. In the second mode of operation the third grating is configured to be positioned at a position other than the third position, and wherein in the second mode of operation the at least some second X-rays produced at the second focal spot avoid the third grating at the position other than the third position.

Thus electronic switching of the position of focal spots, combined with movement of one grating, enables the apparatus to operate, for example, in a DPCI/DFI mode that can operate with an incoherent source and then to be switched to an attenuation mode with reduced mechanical complexity because only one grating of the arrangement is required to be moved.

In an example, in the first mode of operation the at least one X-ray source is configured to produce a third focal spot at a position other than a position of the first focal spot. The at least one X-ray source is configured such that at least some third X-rays produced at the third focal spot pass through the first grating at the first position and pass through the second grating at the second position. The X-ray detector at the detector position is configured to detect the at least some third X-rays.

In this manner, the field of view of the apparatus can be increased in one direction when the apparatus is operating, for example, in a DPCI/DFI mode of operation.

In an example, In the first mode of operation the at least one X-ray source is configured to produce a fourth focal spot at a position other than the position of the first focal spot and at a position other than the position of the third focal spot. The at least one X-ray source is configured such that at least some fourth X-rays produced at the fourth focal spot pass through the first grating at the first position and the pass through the second grating at the second position. The X-ray detector at the detector position is configured to detect the at least some fourth X-rays. An axis between the position of the first focal spot and the position of the third focal spot is orthogonal to an axis between the position of the first focal spot and the position of the fourth focal spot or the axis between the position of the first focal spot and the position of the third focal spot is orthogonal to an axis between the position of the third focal spot and position of the fourth focal spot.

In this manner, the field of view of the apparatus can be increased in two directions when the apparatus is operating in a DPCI/DFI mode of operation.

In an example, the at least one X-ray source comprises two X-ray tubes.

In this manner, the different focal spots at different positions can be effectively and efficiently generated.

In an example, the at least one X-ray source is configured to produce X-rays in the first mode of operation that are characterised by a different spectra of X-ray photon energies to the X-rays produced in the second mode of operation.

In other words, the X-ray spectra of X-rays emitted from the first focal spot, and other focal spots produced in the first mode of operation, is different to the X-ray spectra of X-rays emitted from the second focal spot, and other focal spots produced in the second mode of operation.

The advantage is discussed as follows: current interferometers with "coarse" grating structures raise the difficulty to work with X-rays of short wavelength (high photon energy and tube voltage) and may be limited to operate with a tube voltage of, say 80 kV, whereas, for attenuation imaging it can be most dose efficient for a particular clinical investigation when working with harder X-rays, say at a 120 kV tube voltage. Therefore, the at least one X-ray source configured to produce different X-ray spectra in this manner addresses this.

In an example, the at least one X-ray source is configured to produce X-rays in the first mode of operation that are characterised by a different focal spot point spread function to the X-rays produced in the second mode of operation.

In other words, it can be beneficial to alter the focal spot characteristics with respect to the spatial image resolution achieved and the power rating of the two focal spots. The electron current density in the focal spots may be different and with it the spatial intensity distribution of the X-rays produced. In other words, the point-spread function of the focal spots may be different. E.g. it can be optimal to use a smaller focal spot for DPCI and DFI than for attenuation imaging in order to enhance the visibility for this mode of operation. It can in another situation be more beneficial to use a larger focal spot for DPCI and DFI instead to enhance the X-ray flux, given the limited electrical power density in the focal spot on the anode of a bremsstrahlung source. As some of the gratings absorb photons, the larger input of primary X-rays from the focal spot may avoid photon starvation at the detector and too high a noise level in the image.

In a second aspect, there is provided a system for X-ray imaging an object comprising:
an apparatus for imaging an object according to the first aspect;
a processing unit; and
an output unit. The processing unit is configured to control the apparatus, and is configured to control the output unit. The X-ray detector is configured to provide the processing unit with data relating to the detection of X-rays. The output unit is configured to output data representative of the object.

In an example, the output data comprises attenuation data, and/or phase contrast data, and/or dark field data.

In a third aspect, there is provided a method for X-ray imaging an object, comprising:
positioning an X-ray detector relative to at least one X-ray source such that at least a part of a region between the at least one X-ray source and the X-ray detector is an examination region for accommodating an object;
producing, in a first mode of operation, with the at least one X-ray source a first focal spot, such that at least some first X-rays produced at the first focal spot pass through a first grating of an interferometer arrangement, the first grating positioned at a first position, and such that the at least some first X-rays pass through a second grating of the interferometer arrangement, the second grating positioned at a second position;

detecting, in the first mode of operation, the at least some first X-rays with the X-ray detector at a detector position;

producing, in a second mode of operation, with the at least one X-ray source a second focal spot, such that at least some second X-rays produced at the second focal spot avoid the first grating at the first position; and detecting, in the second mode of operation, the at least some second X-rays with the X-ray detector at the detector position.

According to another aspect, there is provided a computer program element controlling apparatus as previously described which, in the computer program element is executed by processing unit, is adapted to perform the method steps as previously described. According to another example, there is provided a computer readable medium having stored computer element as previously described.

Advantageously, the benefits provided by any of the above aspects and examples equally apply to all of the other aspects and examples and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
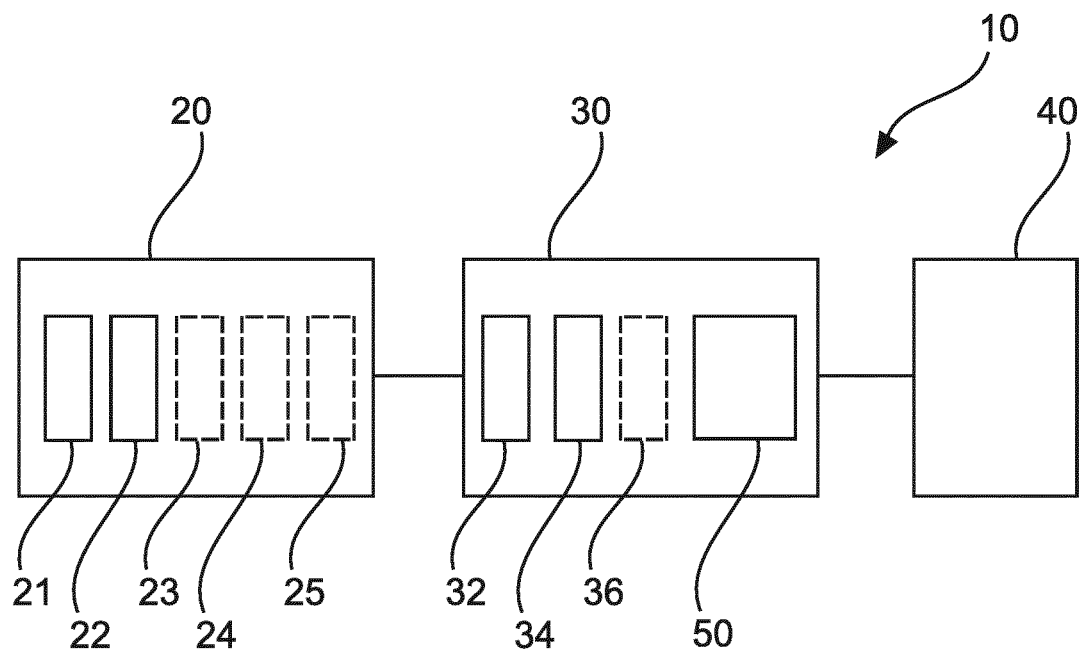
FIG. 1 shows an example of an apparatus for X-ray imaging an object.

FIG. 1 shows an apparatus 10 for X-ray imaging an object. The apparatus 10 comprises at least one X-ray source 20, an X-ray interferometer arrangement 30, and an X-ray detector 40. The X-ray detector 40 is configured to be positioned relative to the at least one X-ray source 20 such that at least a part of a region between the at least one X-ray source 20 and the X-ray detector 40 is an examination region 50 for accommodating an object. The X-ray interferometer arrangement 30 comprises a first grating 32 and a second grating 34. In a first mode of operation the at least one X-ray source 20 is configured to produce a first focal spot 21. The at least one X-ray source 20 is configured to produce X-rays such that at least some first X-rays produced at the first focal spot 21 pass through the first grating 32 at a first position and pass through the second grating 34 at a second position. The X-ray detector 40 at a detector position is configured to detect the at least some first X-rays. In a second mode of operation the at least one X-ray source 20 is configured to produce a second focal spot 22. The at least one X-ray source 20 is configured to produce X-rays such that at least some second X-rays produced at the second focal spot 22 avoid the first grating 32 at the first position. The X-ray detector 40 at the detector position is configured to detect the at least some second X-rays.

In an example, the apparatus is configured to provide differential phase contrast imaging (DPCI). In an example, the apparatus is configured to provide attenuation imaging, relating to the detection of concentration (intensity) values of X-rays with and without the object in the examination region. In an example, the apparatus generates a phase contrast (or differential phase) image, relating to the detection of the phases of the X-rays with and without an object in the examination region. In an example, the apparatus is configured to provide dark field (or de-coherence) imaging, relating to the detection of fringe visibilities of the X-rays with and without an object in the examination region. In an example, the apparatus is configured to provide any combination of these imaging modalities. For example, the apparatus can generate an attenuation image, and generate a phase contrast image, and generate a dark field image.

Further details regarding phase contrast imaging can be found in the publication by Pfeiffer et al., Nature Physics, Vol. 2, 258-261, April 2006; the publication by Roessl et al., Phil. Trans. R. Soc. A. Vol. 372, 1-15, January 2014, and the publication by Weber et al., Medical Physics Letters, Vol. 42(6), 2892-2896, June 2015.

In an example, the interferometer arrangement comprises a Talbot-Lau interferometer. In an example, the interferometer arrangement comprises a diffraction grating configured to modulate onto X-rays emitted by the at least one source an interference pattern detectable by the X-ray detector as X-ray fringes, this can be termed a modulating grating. In an example, the interferometer arrangement comprises another diffraction grating configured to analyze the interference pattern, this can be termed an analysing grating. In an example, the other diffraction grating is an absorption grating. In an example, the two gratings are arranged on mutually opposite sides of the examination region. In an example, the two gratings are arranged on the same side of the examination region. In an example, the interferometer comprises a source grating in addition to the one or two gratings already discussed. In this example, the source grating is located relatively close to the first focal spot and serves to make the X-rays propagating after the source grating partly coherent. In other words, the at least one X-ray source can be adapted so as to emit radiation that is more coherent than if the source grating was not present. Therefore, in some examples a source grating is not required, for example when the X-ray source already produces suitably coherent X-rays. In an example, the interferometer arrangement is configured to produce Moiré fringes. In an example, the interferometer arrangement is purposely detuned such that some fringes are present in the detector area. In an example, the interferometer arrangement is purposely detuned by having a first grating inclined at a small angle to a second grating. In an example, detuning leads to the generation of Moiré fringes on the detector.

In an example, the first grating is a source grating. In an example, the second grating is a modulating grating. In an example, the first grating is a modulating grating. In an example, the second grating is an analysing grating.

In an example, the apparatus in the first mode comprises a scanning arrangement. In an example, scanning comprises movement of the object through the examination region. In an example, scanning comprises movement of the object through the examination region whilst elements of the interferometer arrangement and/or the first focal spot are stationary. In an example, scanning comprises movement of a grating with respect to the first focal spot. In an example, scanning comprises movement of the first focal spot whilst the object is stationary or is not intentionally being moved through the examination region. In an example, scanning comprises movement of one grating with respect to a second grating. In an example, scanning comprises movement of the first grating and movement of the second grating such that the relative positions of the first grating to the second grating does not change. For example, the interferometer arrangement can be translated and/or rotated. In an example, scanning comprises movement of the first focal spot. In an example, scanning comprises movement of the first focal spot whilst elements of the interferometer arrangement are stationary. In other words, movement of the first focal spot, for example laterally, can lead to movement of the projection of the object image on the X-ray detector. For example, there can be a relative shift between the projection of the image and moiré fringes for particular example arrangements. In other words, the apparatus in the first mode can be based on an adaptation of recently proposed scanning phase-contrast and/or dark field systems. However, the apparatus in the first mode can be based on an adaptation of other scanning geometries, in particular the "classical" scanning geometry as implemented on the MicroDose system or in a geometry used by Kottler et al., where the object is moved through a stationary setup of tube, gratings and detector. The apparatus in the first mode can also be based on an adaptation of full-field dark field and/or full field phase contrast systems.

In an example, the at least one X-ray source is configured to emit different intensities of X-rays. In an example, the at least one x-ray source is configured to operated at two different voltages.

In an example, the apparatus has useful application in a clinical environment such as a hospital. In an example, the apparatus can be used for mammography, diagnostic radiology and interventional radiology for the medical examination of patients. In an example, the apparatus has useful application in an industrial environment, for example in non-destructive testing (e.g. analysis as to composition, structure and/or qualities of biological as well non-biological samples) as well as security scanning (e.g. scanning of luggage in airports).

Furthermore, the first and second focal spots can be alternately provided such that the apparatus can easily and quickly switch between the first and second modes of operation, i.e., easily and quickly switch between a DPCI/DFI mode and an attenuation (absorption or radiography) mode of operation.

In an example, in the first mode of operation the first focal spot is configured to be moved by a small distance. Here small means a distance that is smaller than the distance between the first and second focal spot positions. In this manner, image resolution can be improved.

In an example, in the second mode of operation the second focal spot is configured to be moved by a small distance. Here small means a distance that is smaller than the distance between the first and second focal spot positions. In this manner, image resolution can be improved.

In an example, the at least one X-ray source is configured to generate X-rays with different characteristic X-ray spectra. In an example, this is achieved through the provision of different acceleration voltages. In an example, this is achieved through the provision of appropriate filtration, such as having a material filter in the X-ray beam. In an example, this is achieved through the provision of different acceleration voltages in combination with appropriate filtration. In an example, the position of the second focal spot is spaced from the position of the first focal spot by a distance of 1 cm. In examples, the position of the third focal spot is spaced from the position of the first focal spot by an of: 0.5 cm, 1.5 cm, 2 cm, 2.5 cm, 3 cm, 4 cm, 5 cm, 6 cm, 7 cm, 8 cm, 9 cm, 10 cm, 12 cm, 15 cm, 20 cm any distance between these distances.

According to an example, the first grating 32 at the first position is positioned between the examination region 50 and the first focal spot 21.

In an example, the first grating is a source grating configured to make X-rays passing through it partially coherent. In an example, when the X-rays produced at the first focal spot are sufficiently coherent, the first grating is a modulating grating.

According to an example, in the second mode of operation the at least some second X-rays avoid the second grating 34 at the second position.

According to an example, the second grating 34 at the second position is positioned between the first grating 32 at the first position and the examination region 50. According to an example, in the second mode of operation the second grating 34 is configured to be positioned at a position other than the second position. The at least some second X-rays produced at the second focal spot 22 avoid the second grating at the position other than the second position.

In an example, the second grating is fixedly mounted in a suitable frame or cage and this frame is fixedly arranged in a scan arm or other moveable gantry structure. In other words, the second grating can be swung in and out of position such that the apparatus can be operated in both a DPCI mode and in a conventional radiography mode. In the DPCI mode, the arm can be translated or rotated, such that the at least part of an object can be scanned.

According to an example, the X-ray interferometer arrangement 30 comprises a third grating 36. In the first mode of operation the at least some first X-rays produced at the first focal spot 21 pass through the third grating 36 at a third position. In the second mode of operation the third grating 36 is configured to be positioned at a position other than the third position. In the second mode of operation the at least some second X-rays produced at the second focal spot 22 avoid the third grating at the position other than the third position.

In an example, the first grating is a source grating, the second grating is a modulating grating, and the third grating is an analysing grating. In an example, the third grating is positionable between the examination region and the detector. Then, in the second mode of operation the third grating is moved out of the way in order that X-rays do not pass through it and then the apparatus can operate in a conventional attenuation modality.

In an example, the third grating is fixedly mounted in a suitable frame or cage and this frame is fixedly arranged in a scan arm or other moveable gantry structure. In other words, the third grating can be swung in and out of position such that the apparatus can be operated in both a DPCI mode and in a conventional radiography mode. In the DPCI mode, the arm can be translated or rotated, such that the at least part of an object can be scanned.

In an example, the second and third gratings are fixedly mounted with respect to each other in a suitable frame or cage and this frame is fixedly arranged in a scan arm or other moveable gantry structure. In other words, the second and third gratings can be swung in and out of position such that the apparatus can be operated in both a DPCI mode and in a conventional radiography mode. In the DPCI mode, the arm can be translated or rotated, such that the at least part of an object can be scanned.

According to an example, in the first mode of operation the at least one X-ray source 20 is configured to produce a third focal spot 23 at a position other than a position of the first focal spot 21. The at least one X-ray source 20 is configured such that at least some third X-rays produced at the third focal 23 spot pass through the first grating 32 at the first position and pass through the second grating 34 at the second position. The X-ray detector 40 at the detector position is configured to detect the at least some third X-rays.

In an example, the position of the third focal spot is spaced from the position of the first focal spot by a distance of 0.5 mm. In examples, the position of the third focal spot is spaced from the position of the first focal spot by an of: 1 mm, 1.5 mm, 2 mm, 2.5 mm, 3 mm, 3.5 mm, 4 mm, 4.5 mm, 0.5 cm, 1 cm, 2 cm, 3 cm, 5 cm or any distance between these distances.

According to an example, in the first mode of operation the at least one X-ray source 20 is configured to produce a fourth focal spot 24 at a position other than the position of the first focal spot 21 and at a position other than the position of the third focal spot 23. The at least one X-ray source 20 is configured such that at least some fourth X-rays produced at the fourth focal spot 24 pass through the first grating 32 at the first position and the pass through the second grating 34 at the second position. The X-ray detector 40 at the detector position is configured to detect the at least some fourth X-rays. An axis between the position of the first focal spot 21 and the position of the third focal spot 23 is orthogonal to an axis between the position of the first focal spot 21 and the position of the fourth focal spot 24 or the axis between the position of the first focal spot 21 and the position of the third focal spot 23 is orthogonal to an axis between the position of the third focal spot 23 and the position of the fourth focal spot 24.

In an example, the position of the fourth focal spot is spaced from the position of the first focal spot, or the position of the fourth focal spot is spaced from the position of the third focal spot by a distance of 0.5 mm. In examples, the separation is: 1 mm, 1.5 mm, 2 mm, 2.5 mm, 3 mm, 3.5 mm, 4 mm, 4.5 mm, 0.5 cm, 1 cm, 2 cm, 3 cm, 5 cm or any distance between these distances.

In an example, in the second mode of operation the at least one X-ray source is configured to produce a fifth focal spot (25) at a position other than a position of the second focal spot (22), and the at least one X-ray source is configured such that at least some fifth X-rays produced at the fifth focal spot pass avoid the first grating at the first position, wherein the X-ray detector at the detector position is configured to detect the at least some fifth X-rays.

In this manner, the field of view of the apparatus can be increased in one direction when the apparatus is operating in an attenuation mode of operation.

In an example, the position of the fifth focal spot is spaced from the position of the second focal spot by a distance of 0.5 mm. In examples, the position of the fifth focal spot is spaced from the position of the second focal spot by an of: 1 mm, 1.5 mm, 2 mm, 2.5 mm, 3 mm, 3.5 mm, 4 mm, 4.5 mm, 0.5 cm, 1 cm, 2 cm, 3 cm, 5 cm or any distance between these distances.

In an example, in the second mode of operation the at least one X-ray source is configured to produce a sixth focal spot 26 at a position other than the position of the second focal spot 22 and at a position other than the position of the fifth focal spot 25. The at least one X-ray source is configured such that at least some sixth X-rays produced at the sixth focal spot pass avoid the first grating at the first position. The X-ray detector at the detector position is configured to detect the at least some sixth X-rays. An axis between the position of the second focal spot and the position of the fifth focal spot is orthogonal to an axis between the position of the second focal spot and the position of the sixth focal spot or the axis between the position of the second focal spot and the position of the fifth focal spot is orthogonal to an axis between the position of the fifth focal spot and the position of the sixth focal spot.

In this manner, the field of view of the apparatus can be increased in two directions when the apparatus is operating in an attenuation mode of operation.

In an example, the position of the second focal spot is spaced from the position of the sixth focal spot, or the position of the fifth focal spot is spaced from the position of the sixth focal spot by a distance of 0.5 mm. In examples, the separation is: 1 mm, 1.5 mm, 2 mm, 2.5 mm, 3 mm, 3.5 mm, 4 mm, 4.5 mm, 0.5 cm, 1 cm, 2 cm, 3 cm, 5 cm or any distance between these distances.

According to an example, the at least one X-ray source 20 comprises two X-ray tubes.

According to an example, the at least one X-ray source is configured to produce X-rays in the first mode of operation that are characterised by a different spectra of X-ray photon energies to the X-rays produced in the second mode of operation.

In an example, this achieved by using different tube voltages for the acceleration of the electrons which generate braking radiation upon impact on the target. For example, for the focal spot(s) for invoking all the gratings of the interferometer the at least one X-ray source can be operated with electrons of a kinetic energy of 80 keV, whereas the at least one X-ray source when producing the other focal spot(s) for the generation of an attenuation image (which at least avoids the first grating electronically) can operate at 120 keV. By using (at least) two different cathodes this would be achieved by charging the first cathode (DPCI) with 80 kV and the second cathode (for attenuation imaging) with, say, 120 kV.

In an example, the at least one X-ray source comprises two X-ray tubes operating at different voltages.

In an example, the at least one X-ray source rather than using electrons to generate X-rays, uses a different energy source to generate X-rays. For example, X-rays themselves focussed onto a target can produce X-rays, or other light wavelengths can be focussed onto a target to produce X-rays.

According to an example, the at least one X-ray source 20 is configured to produce X-rays in the first mode of operation that are characterised by a different focal spot point spread function to the X-rays produced in the second mode of operation.

Figure 2:
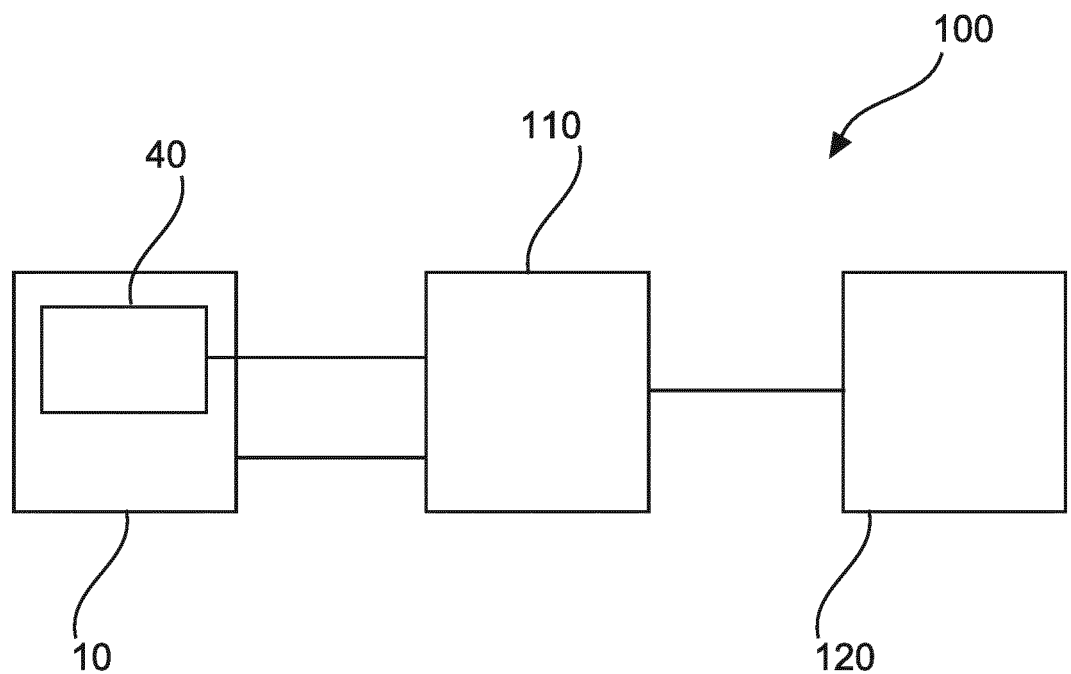
FIG. 2 shows an example of a system for X-ray imaging an object.

FIG. 2 shows a system 100 for X-ray imaging an object. The system 100 comprises an apparatus 10 for imaging an object as described with reference to FIG. 1, a processing unit 110, and an output unit 120. The processing unit 110 is configured to control the apparatus 10, and is configured to control the output unit 120. The X-ray detector 40 is configured to provide the processing unit 110 with data relating to the detection of X-rays. The output unit 120 is configured to output data representative of the object.

In an example, the output unit is configured to output data representative of the X-ray transmission of the at least part of the object.

In an example, the output unit is configured to output data representative of the X-ray the object in the first mode and in the second mode In an example, the output unit is configured to output an absorption (or attenuation) image. In an example, the output unit is configured to output a phase contrast (or differential phase) image. In an example, the output unit is configured to output a dark field image. In an example, the output unit is configured to output any combination of attenuation, phase contrast and dark field images.

According to an example, the output data comprises attenuation data, and/or phase contrast data, and/or dark field data.

Figure 3:
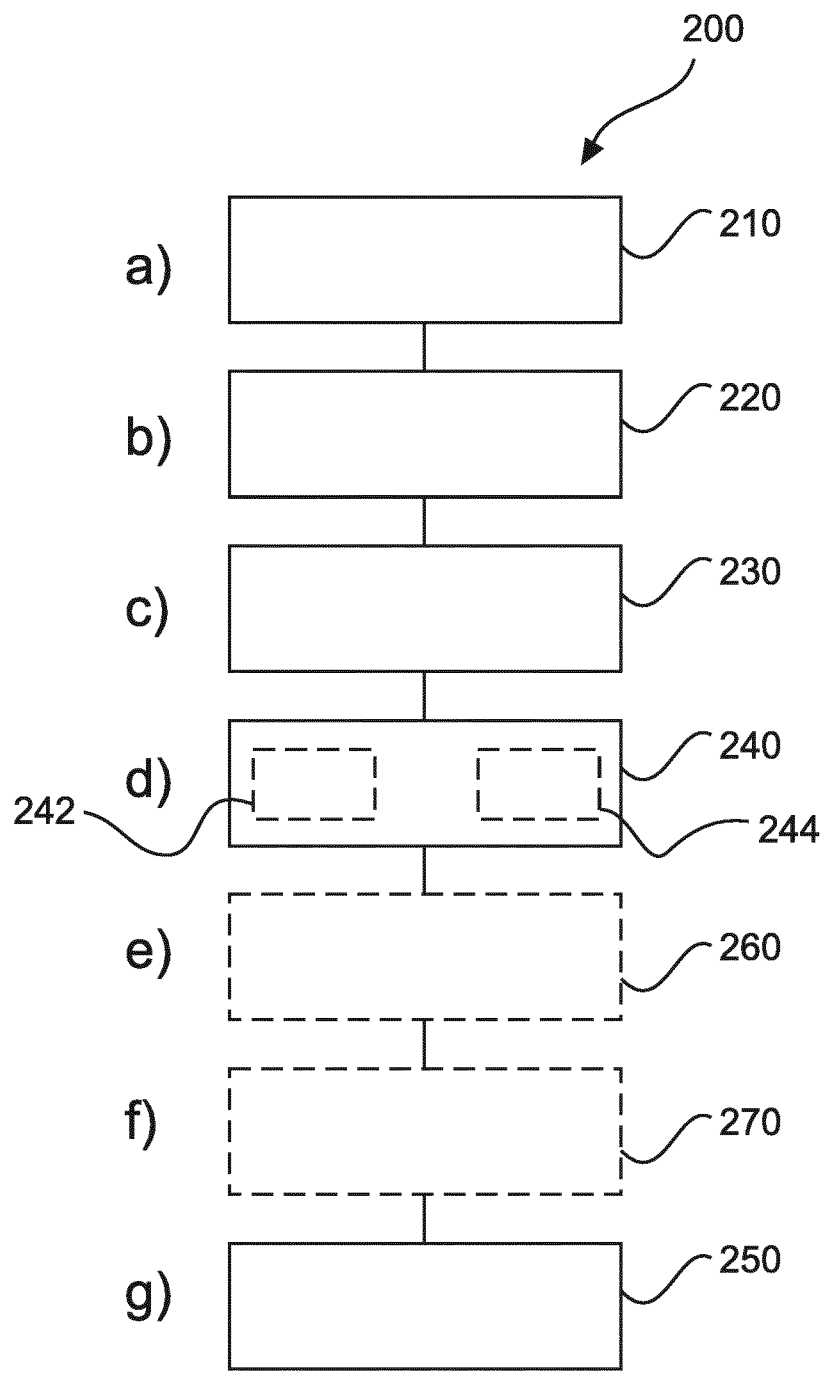
FIG. 3 shows an example of a method for X-ray imaging an object.

FIG. 3 shows a method 200 for X-ray imaging an object in its basic steps. The method 200 comprises:

in a positioning step 210, also referred to as step a), an X-ray detector is positioned relative to at least one X-ray source such that at least a part of a region between the at least one X-ray source and the X-ray detector is an examination region for accommodating an object;

in a producing step 220, also referred to as step b), in a first mode of operation, with the at least one X-ray source a first focal spot is produced, such that at least some first X-rays produced at the first focal spot pass through a first grating of an interferometer arrangement, the first grating positioned at a first position, and such that the at least some first X-rays pass through a second grating of the interferometer arrangement, the second grating positioned at a second position;

in a detecting step 230, also referred to as step c), in the first mode of operation, the at least some first X-rays are detected with the X-ray detector at a detector position;

in a producing step 240, also referred to as step d), in a second mode of operation, with the at least one X-ray source a second focal spot is produced, such that at least some second X-rays produced at the second focal spot avoid the first grating at the first position; and in a detecting step 250, also referred to as step g), in the second mode of operation, the at least some second X-rays are detected with the X-ray detector at the detector position.

In an example of the method, steps b) and d) comprise positioning the first grating at the first position between the examination region and the first focal spot. In an example, step d) comprises the at least some second X-rays avoiding the second grating at the second position.

In an example of the method, steps b) and d) comprise positioning the second grating at the second position between the first grating at the first position and the examination region.

In an example, step d) comprises positioning 242 the second grating at a position other than the second position, and wherein the at least some second X-rays produced at the second focal spot avoid the second grating at the position other than the second position.

In an example, step b) comprises passing the at least some first X-rays produced at the first focal spot pass through a third grating of the interferometer arrangement, the third grating positioned at a third position, and step d) comprises positioning 244 the third grating at a position other than the third position. The at least some second X-rays produced at the second focal spot avoid the third grating at the position other than the third position.

In an example, the method comprises step e): producing 260, in the first mode of operation, with the at least one X-ray source a third focal spot at a position other than a position of the first focal spot, such that at least some third X-rays produced at the third focal spot pass through the first grating at the first position and pass through the second grating at the second position. The X-ray detector at the detector position is configured to detect the at least some third X-rays.

In an example, the method comprises step f): producing 270, in the first mode of operation, with the at least one X-ray source a fourth focal spot at a position other than the position of the first focal spot and at a position other than the position of the third focal spot, such that at least some fourth X-rays produced at the fourth focal spot pass through the first grating at the first position and the pass through the second grating at the second position. The X-ray detector at the detector position is configured to detect the at least some fourth X-rays. An axis between the position of the first focal spot and the position of the third focal spot is orthogonal to an axis between the position of the first focal spot and the position of the fourth focal spot or the axis between the position of the first focal spot and the position of the third focal spot is orthogonal to an axis between the position of the third focal spot and position of the fourth focal spot.

In an example, the method comprises providing data relating to the detection of X-rays, and outputting data representative of the object.

The apparatus, system and method for X-ray imaging an object is now described in further detail with reference to FIGS. 4-6.

Figure 4:
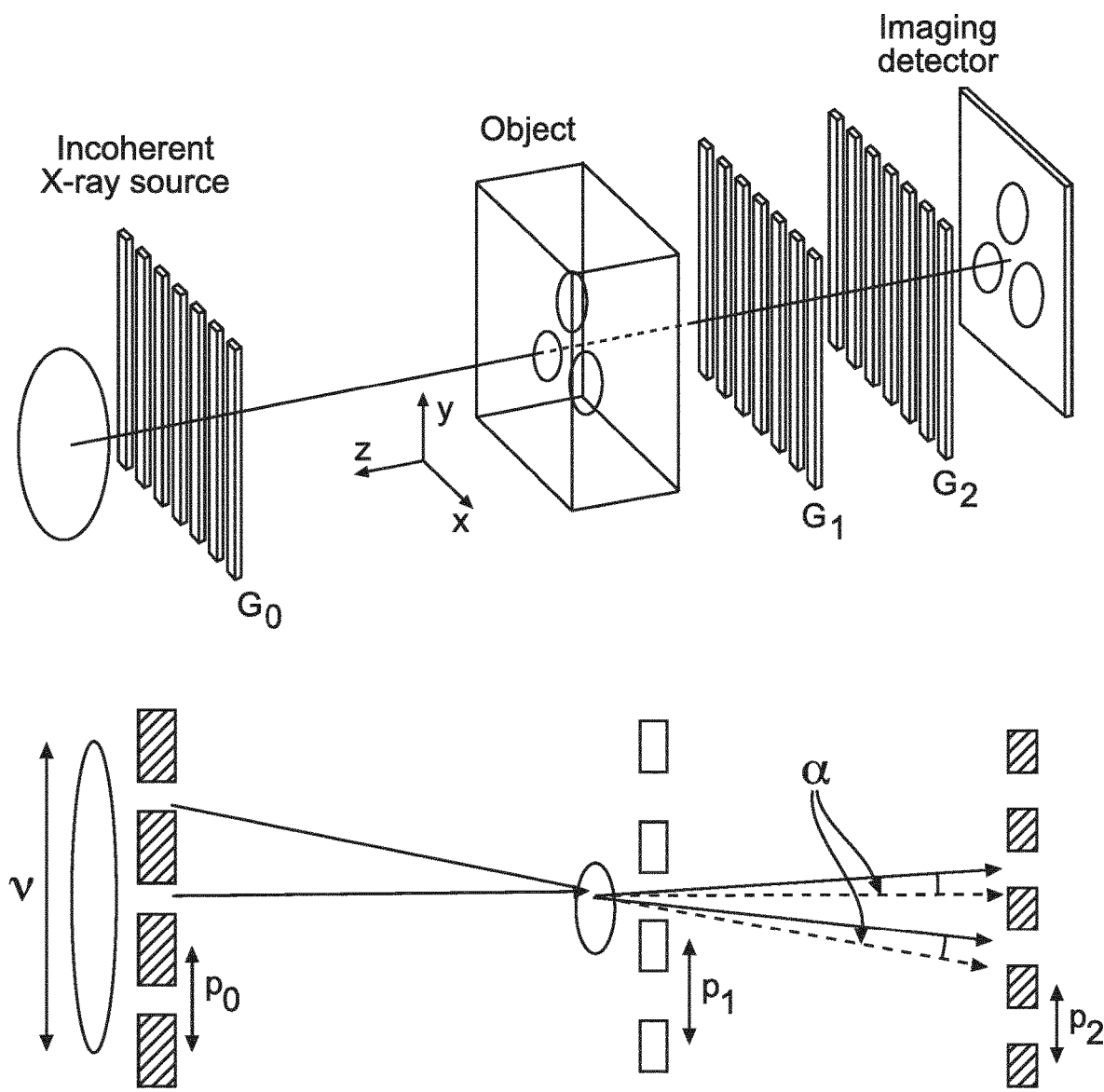
FIG. 4 shows a schematic representation of a Talbot-Lau interferometer for DPCI and DFI.

FIG. 4 shows an example of the apparatus for imaging an object in one mode of operation, where the apparatus is operating in a phase contrast and/or dark field mode. For simplicity the apparatus features relating to a second mode of operation, where the apparatus operates in a normal attenuation or absorption mode of operation, are not shown in FIG. 4. The features relating to the second mode of operation are shown and discussed with respect to FIGS. 5 and 6.

The apparatus shown in FIG. 4 is configured for acquiring X-ray dark field and/or phase contrast images. The apparatus is capable of imaging for the spatial distribution of refraction (phase contrast imaging) and also capable of imaging for the spatial distribution of small angle scattering (dark field imaging) in the object. The apparatus has a grating based interferometer that can be scanned across a stationary X-ray imaging detector. In this example, the interferometer comprises two grating structures G1 and G2, although in other examples a single grating interferometer (having only a single grating G1) is used. In the specific case of a single grating interferometer, the X-ray imaging detector has a pitch sufficiently small, hence a spatial resolution sufficiently large, for detecting i.e. adequately resolving the interference pattern generated by the grating G1 for the purpose of differential phase contrast imaging and/or dark field imaging. For that purpose the X-ray imaging detector may be a high resolution X-ray detector, having for example a spatial resolution of 50 micrometers or more.

In FIG. 4, the grating G1 is either an absorption grating or phase shift grating whereas G2 is an absorption gating. The gratings are manufactured by photo lithographically processing suitable substrates such as a silicon wafer. A pattern of periodic rulings is formed in those silicon "cards" formed by trenches of different aspect ratio. The ruling patterns may be one dimensional but may also be two dimensional such as to confer a checker board pattern.

The apparatus further comprises an X-ray source that has produced an electron beam focal spot on an anode that emits X-rays and the X-ray imaging detector. The X-ray imaging detector can be a 2D full view X-ray detector, which is either planar or curved. A plurality of detector pixels are arranged in rows and columns as an array to form a 2D X-ray radiation sensitive surface capable of registering X-ray radiation emitted by the X-ray source. The X-ray imaging detector and the X-ray source are spaced apart to form an examination region. The examination region is suitably spaced to receive the object to be imaged. The object may be inanimate or animate. For instance the object may be a piece of luggage or other sample to be imaged, or in a medical context the object may be a human or animal patient or at least an anatomic part of a human or animal.

The interferometric grating structures G1 and G2 are arranged in the examination region between the X-ray source and X-ray imaging detector. The X-ray source has a focal spot of lateral extent v from which the X-ray radiation beam emerges. It is the space between the focal spot and the X-ray detector's radiation sensitive surface where the two or three grating structures are arranged. The grating G1 is a phase grating (or modulation grating) and the grating G2 is an analyzer grating. In the apparatus shown in FIG. 4 there is in addition to the interferometric gratings G1, G2 of the interferometer, a further grating G0 which is the source grating.

The source grating G0 is arranged in proximity of the X-ray source focal spot, for example at the exit window of a housing of the X-ray tube. The function of the source grating G0 is to make the emitted radiation at least partly coherent. In other words, the source grating G0 can be dispensed with if an X-ray source is used which is capable of producing coherent radiation.

In operation the at least partly coherent radiation passes through the examination region and interacts with the object. The object then modulates the refraction, and small angle scattering information onto the radiation which can then be extracted by operation of the grating tandem G1 and G2. The gratings G1, G2 induce an interference pattern which can be detected at the X-ray imaging detector as fringes of a Moiré pattern. If there was no object in the examination region, there would still be an interference pattern observable at the X-ray imaging detector, called the reference pattern which is normally captured during a calibration procedure. This comes about by especially adjusting or "de-tuning" the mutual spatial relationship between the two gratings G1 and G2 by inducing a slight flexure for instance so that the two gratings are not perfectly parallel. Now, if the object is positioned in the examination region and interacts with the radiation as mentioned, the Moiré pattern, which is now more appropriately called the object pattern, can be understood as a disturbed version of the reference pattern. This difference from the reference pattern can then be used to compute one or all of the two images (phase contrast, or dark field). This means that the dark field image is acquired at the same time as the phase contrast image. To be able to acquire suitable signals from which the images can be computed, a scanning motion is performed by the grating tandem G1-G2. As a result of this motion, at each pixel of the X-ray imaging detector a series of intensity values are detected. It is to be understood that the mechanical system to effect this scanning motion is very different to a mechanical movement system that is configured to move one or more gratings out of way entirely. For good results, the detuning of the gratings G1, G2 is such that a period of the Moiré pattern should extend for a few of its cycles (two or three) in the direction of the scan motion. For each X-ray detector pixel, the series of intensity values can then be fitted to a (sinusoidal) signal forward model, for example, in order to derive the respective contributions of refraction and small angle scatter. This type of signal processing is done in a signal processing unit not shown in FIG. 4, but which is known to the skilled person. The X-ray imaging detector remains stationary for any given orientation of the optical axis which extend alongs the Z axis. In other words, the X-ray imaging detector is kept stationary (at least during an image acquisition operation) with respect to an arbitrary reference point in the examination region. The interferometric setup as described above is what is commonly referred to as a Talbot-Lau interferometer. The distances between G0 and G1 and between G1 and G2 must be finely tuned to fit the requirements of Talbot distance which in turn is a function of the "pitch" (that is, the spatial period of the grating rulings) of the respective grating. Moving the interferometer relative to the X-ray imaging detector may cause a slight change in fringe distribution due to fringe drift. However, the fringe drift can be compensated by relating such drift to the fringe drift as obtained with a reference scan. Such reference scan may be a blank scan performed at the installation of the X-ray imaging apparatus. This serves to explain one of the problems associated with transforming such a Talbot-Lau interferometer into a conventional absorption or attenuation apparatus, in that in addition to the mechanical complexity of moving gratings out of the way, it is very difficult to place them back in the same positions. The present apparatus mitigates this.

The interferometer can be essentially a "grating pack" with the two gratings G1 and G2 fixedly mounted with respect to each other in a suitable frame or cage and this frame is fixedly arranged in a scan arm or other moveable gantry structure (not shown in FIG. 4). The arm, and with it the interferometer performs a pendulum like motion across the X-ray detector surface. The pivot point for the scan arm motion runs through the focal spot of the X-ray source but does not need to. The gratings G1 and G2 of the interferometer are held in fixed spatial relationship with respect to each other at all times during the scan motion and remain essentially parallel, or at least in a fixed spatial relationship, to G0. However, one or more of the gratings can be independently moved out of the way entirely. Suitable tracking circuitry (not shown) correlates interferometer position with X-ray detector pixel position to timely trigger a sequence of read-out burst to make sure each pixel is supplied with the above mentioned series of measurements to correctly sample the interference pattern. In FIG. 4, the grating G1 is shown on the detector side of the object however it can be equally positioned on the source side of the object.

Figure 5:
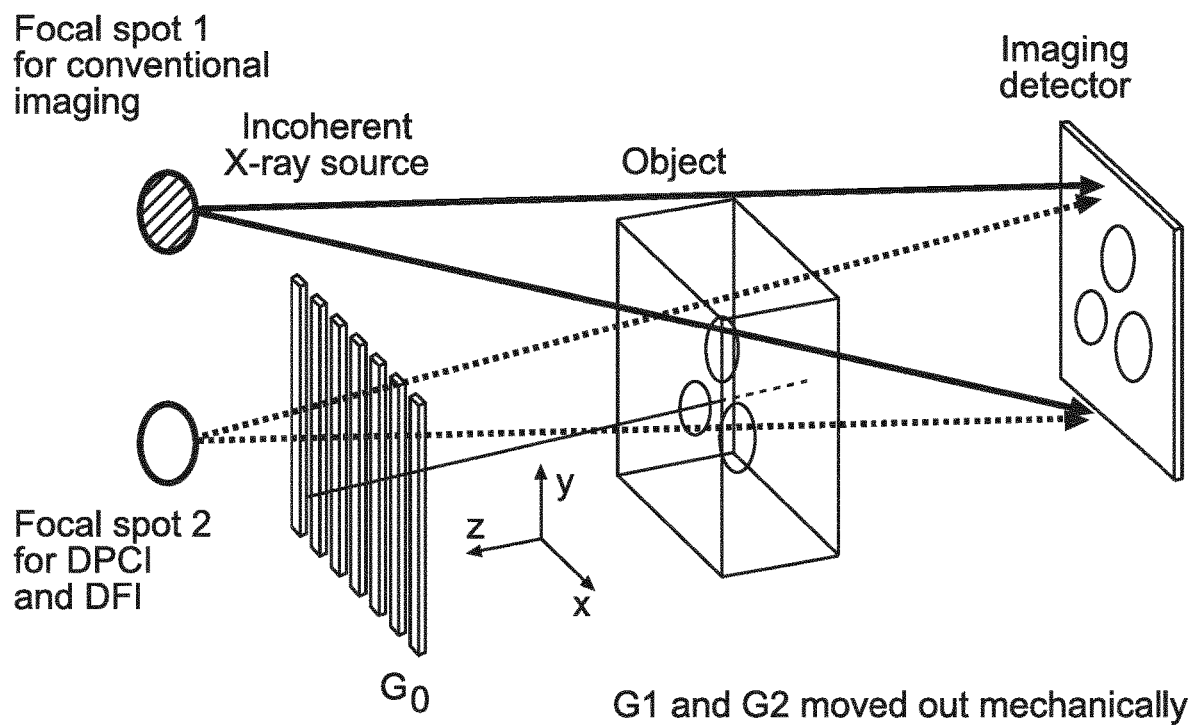
FIG. 5 shows an example of an apparatus for X-ray imaging an object in a one mode of operation.

FIG. 5 shows further detail of the apparatus of FIG. 4, but that is now operating in a different attenuation imaging mode. The X-ray source is comprised of two X-ray tubes, with one X-ray tube producing the focal spot as shown in FIG. 4, which is shown as focal spot 2 in FIG. 5. A second X-ray tube produces a second focal spot, when the first focal spot is not being produced, where the second focal spot is shown as focal spot 1 in FIG. 5. The new focal spot, at focal spot position 1 as shown in FIG. 5, is off to one side of the focal spot used for DPCI/DFI and is used for the conventional attenuation imaging. X-rays produced from the new focal spot, then avoid the source grating G0 but pass through the object and interact with the X-ray imaging detector, without the grating G0 or the detector requiring to be moved. In FIG. 5, the gratings G1 and G2 have been moved out of the way mechanically. In the embodiment where grating G1 is on the detector side of the object when correctly sized and positioned and with correct positioning of the focal spots the X-rays pass through all gratings G0, G1 and G2 in the DPCI/DFI mode, but avoid gratings G0 and G1 in the attenuation mode without those gratings having to be moved. In this way, the system is made more mechanical simple as fewer elements have to be moved out of the way and then moved back. Additionally, alignment becomes more easily managed because a reduced number of elements need to be moved completely out of the way, with the other non-moved elements then being fixed relatively one to the other. As discussed above, the apparatus can dispense with grating G2 and in this arrangement, with G0 and G1 on the source side of the object, no gratings need to be moved and the apparatus can switch from a DPCI/DFI mode to an attenuation mode, and back again, simply through the electronic switching of the position of the electron focal spot from which X-rays are emitted. The electronic switching can be provided by electric or magnetic means like grid switching or magnetic deflection of an electron beam or by any combination thereof.

Figure 6:
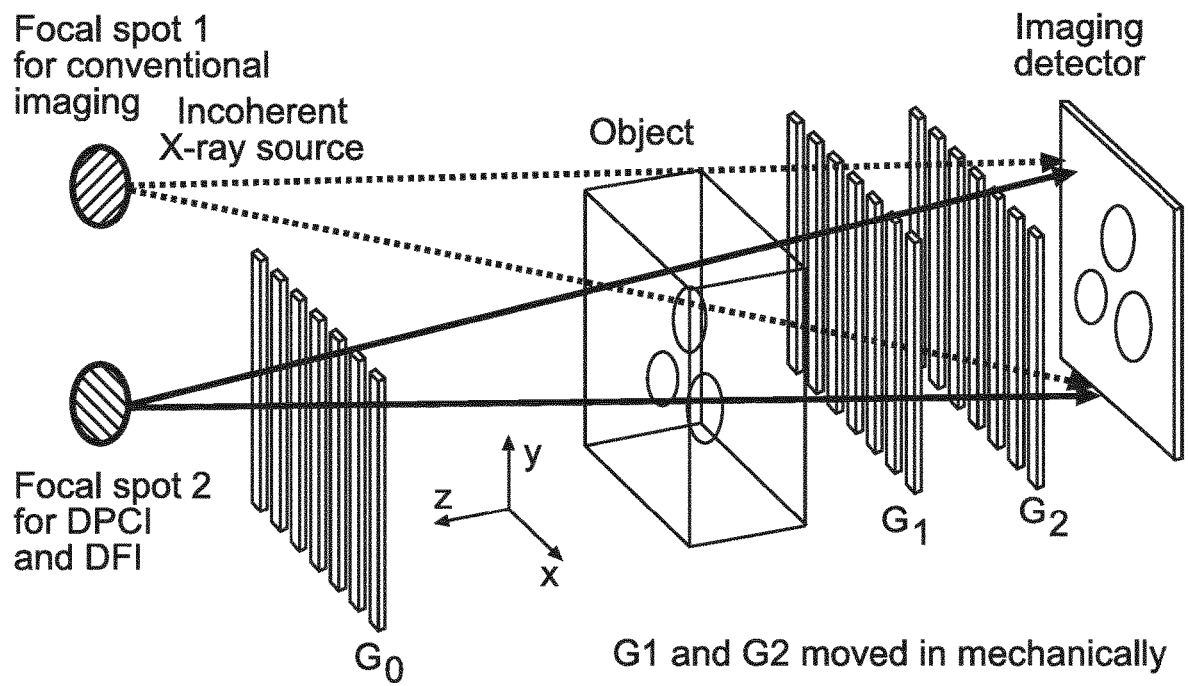
FIG. 6 shows an example of the apparatus of FIG. 5 in another mode of operation.

FIG. 6 then shows the apparatus with the gratings moved back into position, where the X-ray source is producing the electron focal spot at original position again, such that the apparatus is again operating in a DPCI/DFI mode. As discussed above, in the shown embodiment two gratings need to be moved, but in another embodiment only one grating needs to be moved, and in another embodiment no gratings need to be moved.

In this manner, by electronically switching the focused electron beam position X-rays can be made to avoid one or two gratings, which can be remain fixed in position along with the detector.

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for X-ray imaging an object, comprising:
   at least one X-ray source;
   an X-ray interferometer arrangement;
   an X-ray detector;
   wherein; the X-ray detector is configured to be positioned relative to the at least one X-ray source, such that at least a part of a region between the at least one X-ray source and the X-ray detector is an examination region for accommodating the object;
   wherein the X-ray interferometer arrangement comprises a first grating and a second grating;
   wherein in a first mode of operation the at least one X-ray source is configured to produce a first focal spot, and the at least one X-ray source is configured to produce X-rays, such that at least some first X-rays produced at the first focal spot pass through the first grating at a first position and pass through the second grating at a second position, wherein the X-ray detector is configured to detect the at least some first X-rays; and
   wherein in a second mode of operation the at least one X-ray source is configured to produce a second focal spot, and the at least one X-ray source is configured to produce X-rays, such that at least some second X-rays produced at the second focal spot avoid the first grating at the first position, wherein the X-ray detector is configured to detect the at least some second X-rays.

2. The apparatus according to claim 1, wherein the first grating at the first position is positioned between the examination region and the first focal spot.

3. The apparatus according to claim 1, wherein in the second mode of operation the at least some second X-rays avoid the second grating at the second position.

4. The apparatus according to claim 1, wherein the second grating at the second position is positioned between the first grating at the first position and the examination region.

5. The apparatus according to claim 1, wherein in the second mode of operation the second grating is configured to be positioned at a position other than the second position, and wherein the at least some second X-rays produced at the second focal spot avoid the second grating at the position other than the second position.

6. The apparatus according to claim 1, wherein the X-ray interferometer arrangement comprises a third grating, wherein in the first mode of operation the at least some first X-rays produced at the first focal spot pass through the third grating at a third position, and wherein in the second mode of operation the third grating is configured to be positioned at a position other than the third position, and wherein in the second mode of operation the at least some second X-rays produced at the second focal spot avoid the third grating at the position other than the third position.

7. The apparatus according to claim 1, wherein in the first mode of operation the at least one X-ray source is configured to produce a third focal spot at a position other than a position of the first focal spot, and the at least one X-ray source is configured such that at least some third X-rays produced at the third focal spot pass through the first grating at the first position and pass through the second grating at the second position, wherein the X-ray detector is configured to detect the at least some third X-rays.

8. The apparatus according to claim 7, wherein in the first mode of operation the at least one X-ray source is configured to produce a fourth focal spot at a position other than the position of the first focal spot and at the position other than the position of the third focal spot, and the at least one X-ray source is configured such that at least some fourth X-rays produced at the fourth focal spot pass through the first grating at the first position and the pass through the second grating at the second position, wherein the X-ray detector is configured to detect the at least some fourth X-rays, and wherein an axis between the position of the first focal spot and the position of the third focal spot is orthogonal to an axis between the position of the first focal spot and the position of the fourth focal spot, or the axis between the position of the first focal spot and the position of the third focal spot is orthogonal to an axis between the position of the third focal spot and the position of the fourth focal spot.

9. The apparatus according to claim 1, wherein the at least one X-ray source comprises two X-ray tubes.

10. The apparatus according to claim 1, wherein the at least one X-ray source is configured to produce X-rays in the first mode of operation that are characterized by a different spectra of X-ray photon energies to the X-rays produced in the second mode of operation.

11. The apparatus according to claim 1, wherein the at least one X-ray source is configured to produce X-rays in the first mode of operation that are characterized by a different focal spot point spread function to the X-rays produced in the second mode of operation.

12. A system for X-ray imaging an object, comprising:
an apparatus for imaging an object comprising:
at least one X-ray source;
an X-ray interferometer arrangement;
an X-ray detector;
wherein the X-ray detector is configured to be positioned relative to the at least one X-ray source such that at least a part of a region between the at least one X-ray source and the X-ray detector is an examination region for accommodating the object;
wherein the X-ray interferometer arrangement comprises a first grating and a second grating;
wherein in a first mode of operation the at least one X-ray source is configured to produce a first focal spot, and the at least one X-ray source is configured to produce X-rays such that at least some first X-rays produced at the first focal spot pass through the first grating at a first position and pass through the second grating at a second position, wherein the X-ray detector is configured to detect the at least some first X-rays; and
wherein in a second mode of operation the at least one X-ray source is configured to produce a second focal spot, and the at least one X-ray source is configured to produce X-rays such that at least some second X-rays produced at the second focal spot avoid the first grating at the first position, wherein the X-ray detector is configured to detect the at least some second X-rays;
a processor; and
an output unit;
wherein the processor is configured to control the apparatus and the output unit;
wherein the X-ray detector is configured to provide the processor with data relating to the detection of X-rays; and
wherein the output unit is configured to output data representative of the object.

13. The system according to claim 12, wherein the output data comprises at least one of attenuation data, phase contrast data, and dark field data.

14. A method for X-ray imaging an object, comprising:
positioning an X-ray detector relative to at least one X-ray source, such that at least a part of a region between the at least one X-ray source and the X-ray detector is an examination region for accommodating an object;
producing, by the at least one X-ray source in a first mode of operation, a first focal spot, such that at least some first X-rays produced at the first focal spot pass through a first grating of an interferometer arrangement, the first grating positioned at a first position, and such that the at least some first X-rays pass through a second grating of the interferometer arrangement, the second grating positioned at a second position;
detecting, by the X-ray detector in the first mode of operation, the at least some first X-rays;
producing, by the at least one X-ray source in a second mode of operation, a second focal spot, such that at least some second X-rays produced at the second focal spot avoid the first grating at the first position; and
detecting, by the X-ray detector in the second mode of operation, the at least some second X-rays.

15. A non-transitory computer-readable medium having one or more executable instructions stored thereon, which when executed by a processor, cause the processor to perform a method for X-ray imaging an object, the method comprising:
positioning an X-ray detector relative to at least one X-ray source such that at least a part of a region between the at least one X-ray source and the X-ray detector is an examination region for accommodating an object;

producing, by the at least one X-ray source in a first mode of operation, a first focal spot, such that at least some first X-rays produced at the first focal spot pass through a first grating of an interferometer arrangement, the first grating positioned at a first position, and such that the at least some first X-rays pass through a second grating of the interferometer arrangement, the second grating positioned at a second position;

detecting, by the X-ray detector in the first mode of operation, the at least some first X-rays;

producing, by the at least one X-ray source in a second mode of operation, a second focal spot, such that at least some second X-rays produced at the second focal spot avoid the first grating at the first position; and detecting, by the X-ray detector in the second mode of operation, the at least some second X-rays.

\* \* \* \* \*